United States Patent
Ashrafzadeh et al.

(10) Patent No.: US 8,522,452 B2
(45) Date of Patent: Sep. 3, 2013

(54) LAUNDRY TREATING APPLIANCE WITH STATE OF DRYNESS BASED IMAGING CONTROL

(75) Inventors: Farhad Ashrafzadeh, Stevensville, MI (US); James P. Carow, Saint Joseph, MI (US); Shreecharan Kanchanavally, Lisle, IL (US); Sathish Andrea Sundaram, Benton Harbor, MI (US)

(73) Assignee: Whirlpool Corporation, Benton Harbor, MI (US)

( * ) Notice: Subject to any disclaimer, the term of this patent is extended or adjusted under 35 U.S.C. 154(b) by 997 days.

(21) Appl. No.: 12/388,743

(22) Filed: Feb. 19, 2009

(65) Prior Publication Data

US 2010/0205823 A1    Aug. 19, 2010

(51) Int. Cl.
- F26B 19/00   (2006.01)
- F26B 13/10   (2006.01)
- G06K 9/00    (2006.01)

(52) U.S. Cl.
USPC ............ 34/524; 34/529; 34/88; 382/111

(58) Field of Classification Search
USPC .......... 34/445, 524, 529, 449, 88, 560, 130; 8/137; 356/914; 73/1.56; 382/107, 111; 725/12; 700/259, 275; 116/213
See application file for complete search history.

(56) References Cited

U.S. PATENT DOCUMENTS

| | | | |
|---|---|---|---|
| 5,345,060 A | 9/1994 | Hazan et al. | |
| 5,391,890 A | 2/1995 | Migliorini | |
| 5,755,041 A | 5/1998 | Horwitz | |
| 6,026,592 A | 2/2000 | Herr | |
| 6,488,155 B2 | 12/2002 | Lawandy et al. | |
| 7,200,511 B2* | 4/2007 | Damrath | 702/127 |
| 7,363,780 B2 | 4/2008 | Lee et al. | |
| 7,415,781 B2* | 8/2008 | Barron et al. | 34/595 |
| 2001/0049846 A1 | 12/2001 | Guzzi et al. | |
| 2002/0118366 A1 | 8/2002 | Baldwin | |
| 2003/0034443 A1 | 2/2003 | Kouznetsov et al. | |
| 2004/0249843 A1 | 12/2004 | Damrath | |
| 2005/0004956 A1 | 1/2005 | Pourdeyhimi | |
| 2005/0196046 A1 | 9/2005 | Hudnut et al. | |
| 2006/0243931 A1 | 11/2006 | Haran et al. | |
| 2006/0255300 A1 | 11/2006 | Shakespeare | |
| 2007/0272272 A1 | 11/2007 | Choi et al. | |
| 2008/0013818 A1 | 1/2008 | Shakespeare | |
| 2008/0276964 A1 | 11/2008 | Hendrickson et al. | |
| 2009/0211109 A1* | 8/2009 | Choi et al. | 34/491 |

FOREIGN PATENT DOCUMENTS

| | | | |
|---|---|---|---|
| DE | 3938822 A1 | 5/1991 | |
| DE | 19961459 A1 | 7/2001 | |
| DE | 10156157 A1 | 5/2003 | |
| DE | 10302866 A1 | 8/2004 | |
| DE | 102005055411 A1 | 5/2007 | |
| EP | 0544945 A1 | 6/1993 | |
| FR | 2894996 A1 | 6/2007 | |
| JP | 04012799 A | 1/1992 | |

(Continued)

*Primary Examiner* — Kenneth Rinehart
*Assistant Examiner* — John McCormack
(74) *Attorney, Agent, or Firm* — Clifton G. Green; McGarry Bair PC (57) ABSTRACT

The invention relates to a method of operating a laundry treating appliance having a rotatable drum defining a laundry treating chamber. The laundry in the laundry treating chamber may be imaged and a state of dryness of the laundry determined based on the imaging of the laundry. The operation of the laundry treating appliance may be based on the determined state of dryness.

51 Claims, 7 Drawing Sheets

(56) References Cited

FOREIGN PATENT DOCUMENTS

| | | | | |
|---|---|---|---|---|
| JP | 04244193 A | * | 9/1992 | |
| JP | 4244193 A | | 9/1992 | |
| JP | 05200194 A | * | 8/1993 | |
| JP | 10-277292 A | | 10/1998 | |
| JP | 2002224486 A | | 8/2002 | |
| JP | 2007-221811 A | | 8/2007 | |
| JP | 2008054960 A | | 3/2008 | |
| WO | 89/04887 A1 | | 6/1989 | |
| WO | 01/78573 A2 | | 10/2001 | |
| WO | 2008/000812 A1 | | 1/2008 | |

* cited by examiner

LAUNDRY TREATING APPLIANCE WITH STATE OF DRYNESS BASED IMAGING CONTROL

BACKGROUND OF THE INVENTION

Laundry treating appliances, such as clothes washers, clothes dryers, refreshers, and non-aqueous systems, may have a configuration based on a rotating drum that defines a treating chamber in which laundry items are placed for treatment. The laundry treating appliance may have a controller that implements a number of pre-programmed cycles of operation. The user typically manually selects the cycle of operation from the given pre-programmed cycles. Each pre-programmed cycle may have any number of adjustable parameters, which may be input by the user or may be set by the controller. The controller may set the parameter according to default values, predetermined values, or responsive to conditions within the treating chamber.

SUMMARY OF THE INVENTION

The invention relates to a method of determining a state of dryness of the laundry based on image data of the laundry located in a treating chamber of a laundry treating appliance.

DESCRIPTION OF EMBODIMENTS OF THE INVENTION

Figure 1:
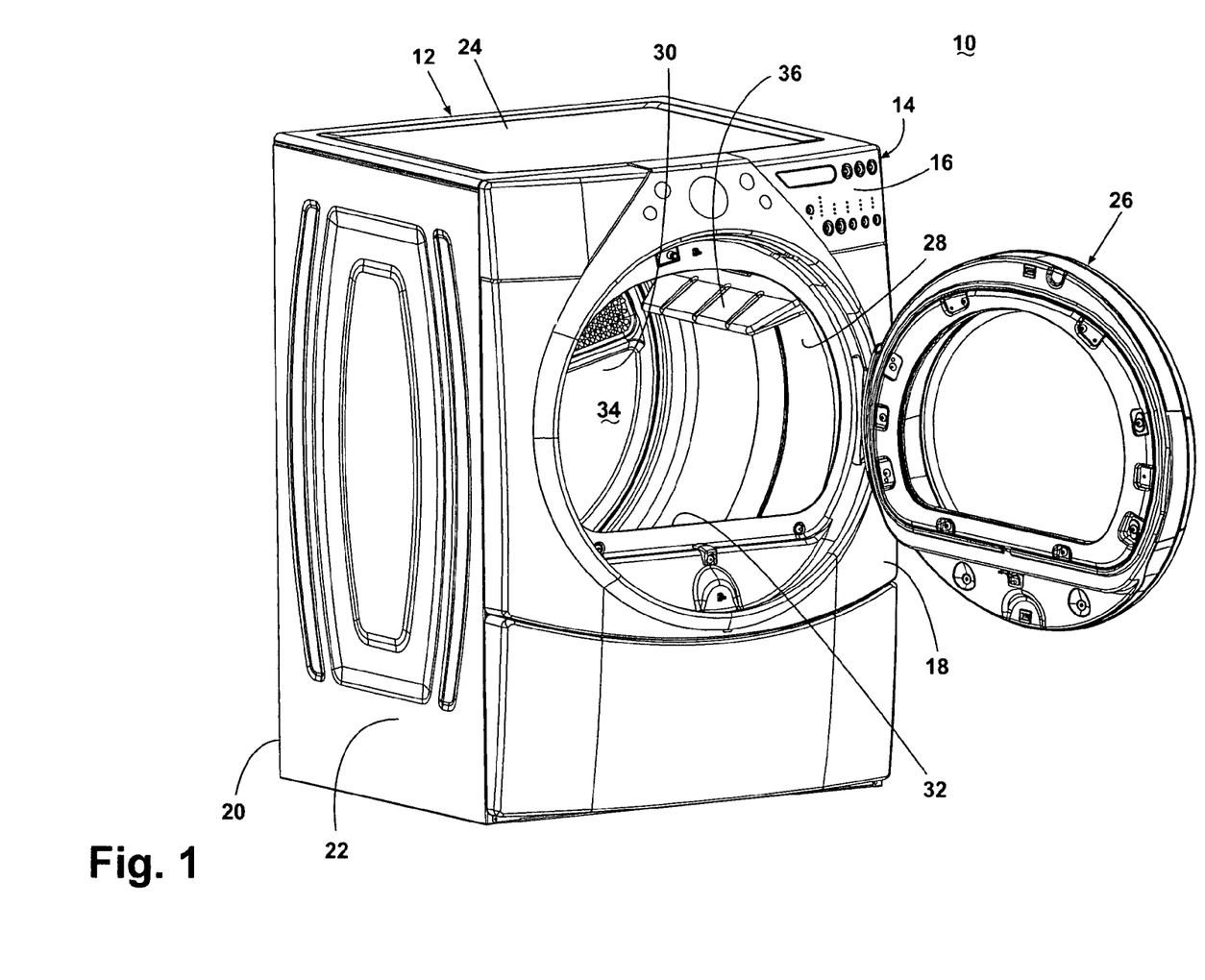
FIG. 1 is a front perspective view of a laundry treating appliance in the form of a clothes dryer with a treating chamber according to one embodiment of the invention.

FIG. 1 illustrates one embodiment of a laundry treating appliance in the form of a clothes dryer 10 according to the invention. While the laundry treating appliance is illustrated as a clothes dryer 10, the laundry treating appliance according to the invention may be any appliance which performs a cycle of operation on laundry, non-limiting examples of which include a horizontal or vertical axis clothes washer; a combination washing machine and dryer; a tumbling or stationary refreshing/revitalizing machine; an extractor; a non-aqueous washing apparatus; and a revitalizing machine. The clothes dryer 10 described herein shares many features of a traditional automatic clothes dryer, which will not be described in detail except as necessary for a complete understanding of the invention.

As illustrated in FIG. 1, the clothes dryer 10 may include a cabinet 12 in which is provided a controller 14 that may receive input from a user through a user interface 16 for selecting a cycle of operation and controlling the operation of the clothes dryer 10 to implement the selected cycle of operation.

The cabinet 12 may be defined by a front wall 18, a rear wall 20, and a pair of side walls 22 supporting a top wall 24. A door 26 may be hingedly mounted to the front wall 18 and may be selectively moveable between opened and closed positions to close an opening in the front wall 18, which provides access to the interior of the cabinet.

Figure 2:
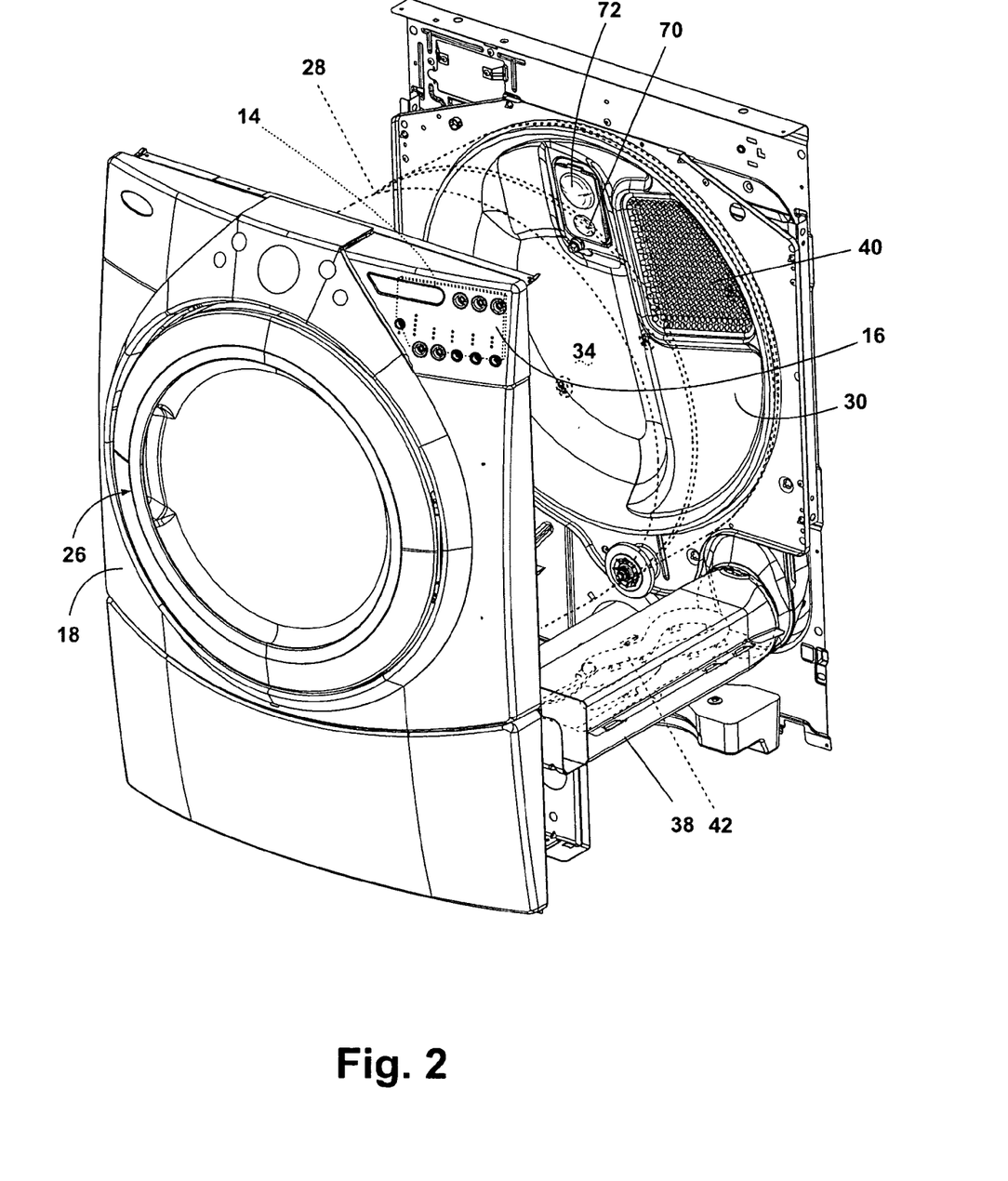
FIG. 2 is a partial perspective view of the dryer of FIG. 1 with portions of the cabinet removed for clarity according to one embodiment of the invention.

A rotatable drum 28 may be disposed within the interior of the cabinet 12 between opposing stationary rear and front bulkheads 30 and 32, which collectively define a treating chamber 34, for treating laundry, having an open face that may be selectively closed by the door 26. Examples of laundry include, but are not limited to, a hat, a scarf, a glove, a sweater, a blouse, a shirt, a pair of shorts, a dress, a sock, a pair of pants, a shoe, an undergarment, and a jacket. Furthermore, textile fabrics in other products, such as draperies, sheets, towels, pillows, and stuffed fabric articles (e.g., toys), may be dried in the clothes dryer 10.

The drum 28 may include at least one lifter 36. In most dryers, there are multiple lifters. The lifters 36 may be located along the inner surface of the drum 28 defining an interior circumference of the drum 28. The lifters 36 facilitate movement of the laundry within the drum 28 as the drum 28 rotates.

Still referring to FIG. 2, an air flow system for the clothes dryer 10 according to one embodiment of the invention will now be described. The air flow system supplies air to the treating chamber 34 and then exhausts air from the treating chamber 34. The supplied air may be heated or not. The air flow system may have an air supply portion that may be formed in part by an inlet conduit 38, which has one end open to the ambient air and another end fluidly coupled to an inlet grill 40, which may be in fluid communication with the treating chamber 34. A heating element 42 may lie within the inlet conduit 38 and may be operably coupled to and controlled by the controller 14. If the heating element 42 is turned on, the supplied air will be heated prior to entering the drum 28.

Figure 3:
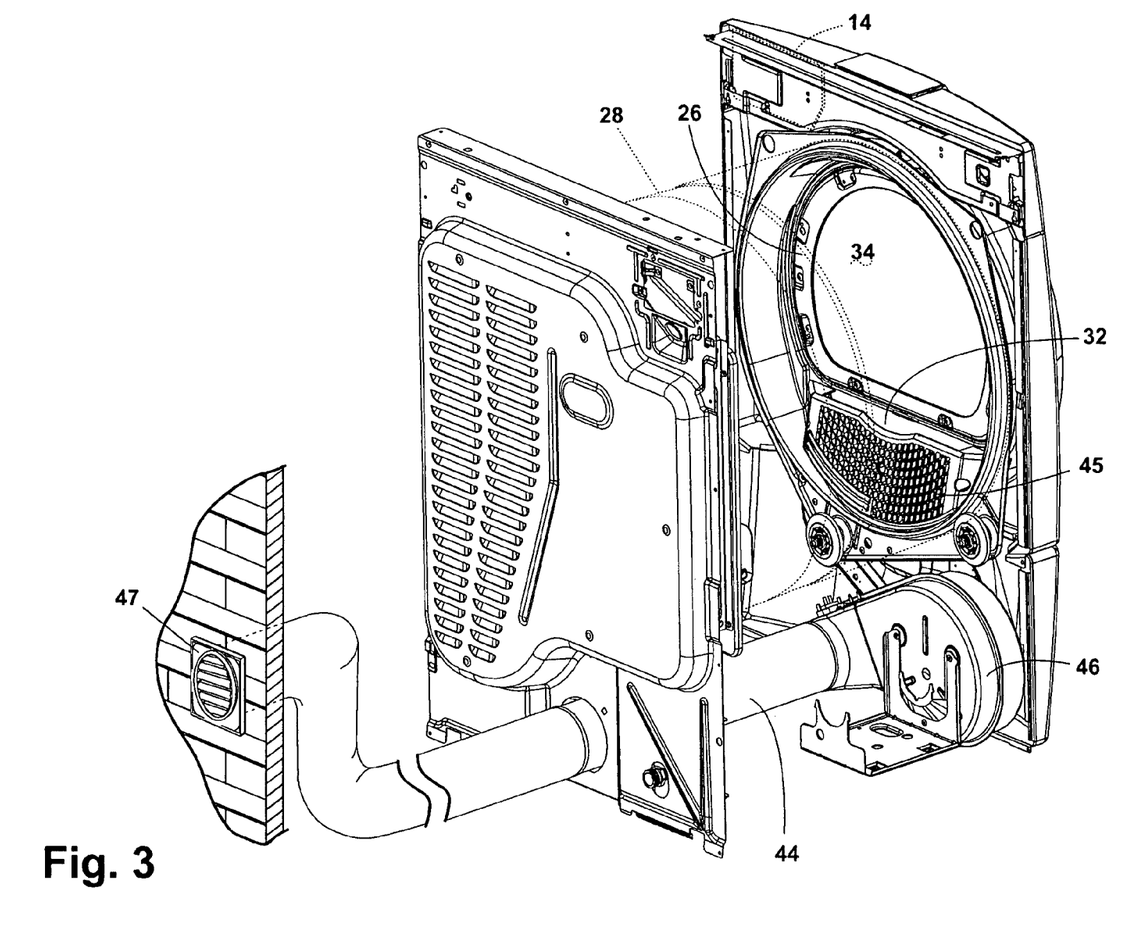
FIG. 3 is second partial perspective view of the dryer of FIG. 1 with portions of the cabinet removed for clarity according to one embodiment of the invention.

Referring to FIG. 3, the air supply system may further include an air exhaust portion that may be formed in part by an exhaust conduit 44 and lint trap 45, which are fluidly coupled by a blower 46. The blower 46 may be operably coupled to and controlled by the controller 14. Operation of the blower 46 draws air into the treating chamber 34 as well as exhausts air from the treating chamber 34 through the exhaust conduit 44. The exhaust conduit 44 may be fluidly coupled with a household exhaust duct 47 for exhausting the air from the drying chamber to the outside.

Figure 4:
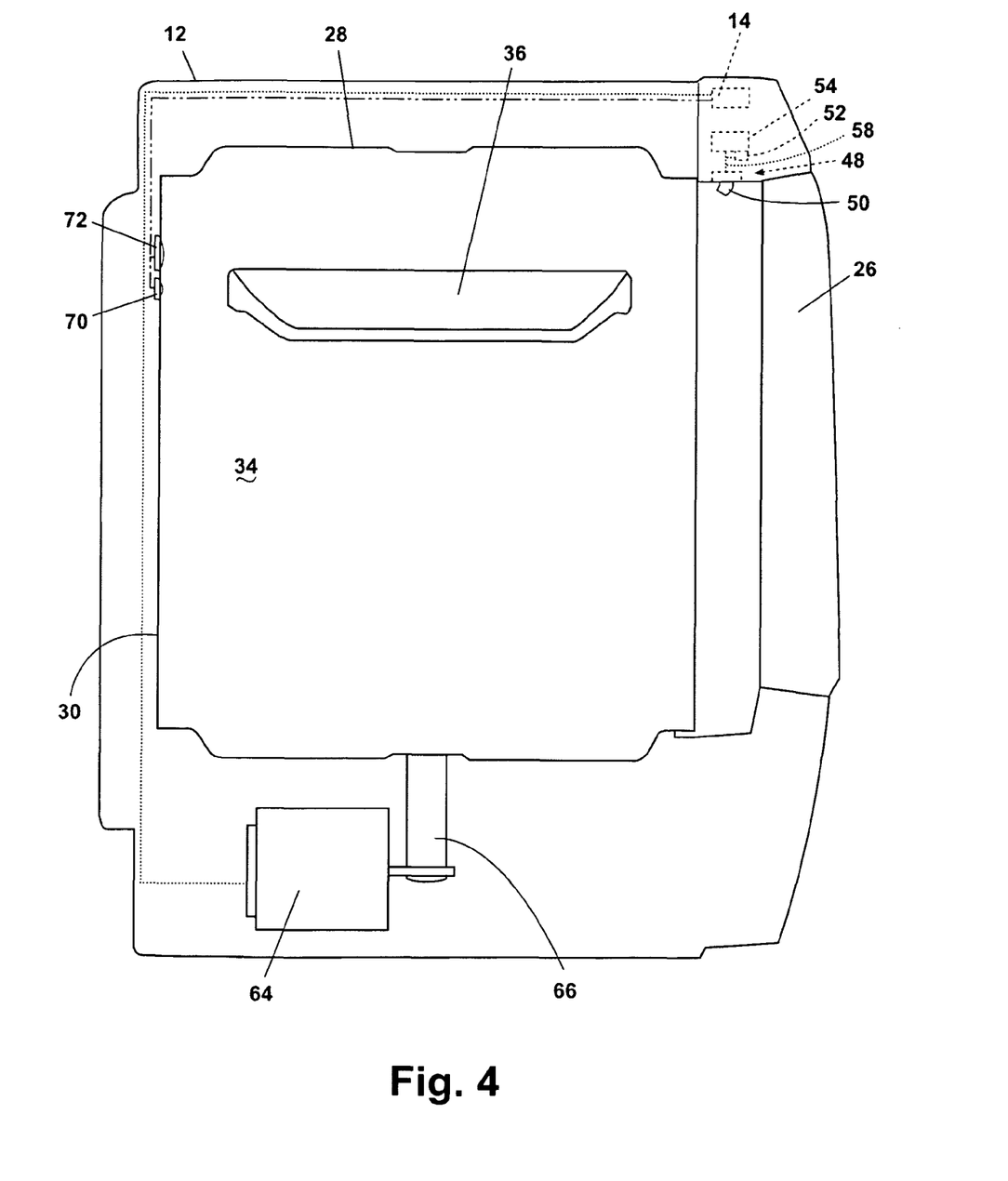
FIG. 4 is a schematic side view of the dryer of FIG. 1 having an imaging system for imaging the treating chamber the dryer according to one embodiment of the invention.

Referring now to FIG. 4, the clothes dryer 10 may optionally have a dispensing system 48 for dispensing treating chemistries, including without limitation water or steam, into the treating chamber 34, and thus may be considered to be a dispensing dryer. The dispensing system 48 may include a reservoir 54 capable of holding treating chemistry and a dispenser 50 that fluidly couples with the reservoir 54 through a dispensing line 58. The treating chemistry may be delivered to the dispenser 50 from the reservoir 54 and the dispenser 50 may dispense the chemistry into the treating chamber 34. The dispenser 50 may be positioned to direct the treating chemistry at the inner surface of the drum 28 so that laundry may contact and absorb the chemistry, or to dispense the chemistry directly onto the laundry in the treating chamber 34. The type of dispenser 50 is not germane to the invention. A chemistry meter 52 may electronically couple, wired or wirelessly, to the controller 14 to control the amount of treating chemistry dispensed.

As is typical in a clothes dryer, the drum 28 may be rotated by a suitable drive mechanism, which is illustrated as a motor 64 and a coupled belt 66. The motor 64 may be operably coupled to the controller 14 to control the rotation of the drum 28 to complete a cycle of operation. Other drive mechanisms, such as direct drive, may also be used.

The clothes dryer 10 may also have an imaging device 70 to image the treating chamber 34 and/or anything within the treating chamber 34. Exemplary imaging devices 70 may include any optical sensor capable of capturing still or moving images, such as a camera. One suitable type of camera is a CMOS camera. Other exemplary imaging devices include a CCD camera, a digital camera, a video camera or any other type of device capable of capturing an image. That camera may capture either or both visible and non-visible radiation. For example, the camera may capture an image using visible light. In another example, the camera may capture an image using non-visible light, such as ultraviolet light. In yet another example, the camera may be a thermal imaging device capable of detecting radiation in the infrared region of the electromagnetic spectrum. The imaging device 70 may be located on either of the rear or front bulkhead 30, 32 or in the door 26. It may be readily understood that the location of the imaging device 70 may be in numerous other locations depending on the particular structure of the dryer and the desired position for obtaining an image. There may also be multiple imaging devices, which may image the same or different areas of the treating chamber 34.

The clothes dryer 10 may also have an illumination source 72. The type of illumination source 72 may vary. In one configuration, the illumination source 72 may be a typical incandescent dryer light which is commonly used to illuminate the treating chamber 34. Alternatively, one or more LED lights may be used in place of an incandescent bulb. The illumination source 72 may also be located behind the rear bulkhead 30 of the drum 28 such that the light shines through the holes of the air inlet grill 40. It is also within the scope of the invention for the clothes dryer 10 to have more than one illumination source 72. For example, an array of LED lights may be placed at multiple positions in either bulkhead 30, 32.

The illumination source 72 may be located on the same side of the drum 28 as the imaging device 70, as illustrated in FIG. 4, or located on a different side of the drum 28. When the illumination source 72 is located on the same side of the drum 28 as the imaging device 70, the imaging device 70 may detect the light that may be reflected by the drum 28 and the laundry load. Image analysis may then be used to separate the drum 28 from the laundry load. When the illumination source 72 is located on a side of the drum 28 opposite the imaging device 70, the imaging device 70 detects only the light from the illumination source 72 that is not blocked by the laundry load. At any instant in time, a given location in an image will be dark or light depending on whether or not laundry is present at that location.

The illumination generated by the illumination source may vary, and may well be dependent on the type of imaging device. For example, illumination may be infrared if the imaging device is configured to image the infrared spectrum. Similarly, the illumination may be visible light, if the imaging device is configured to image the visible spectrum.

Figure 5:
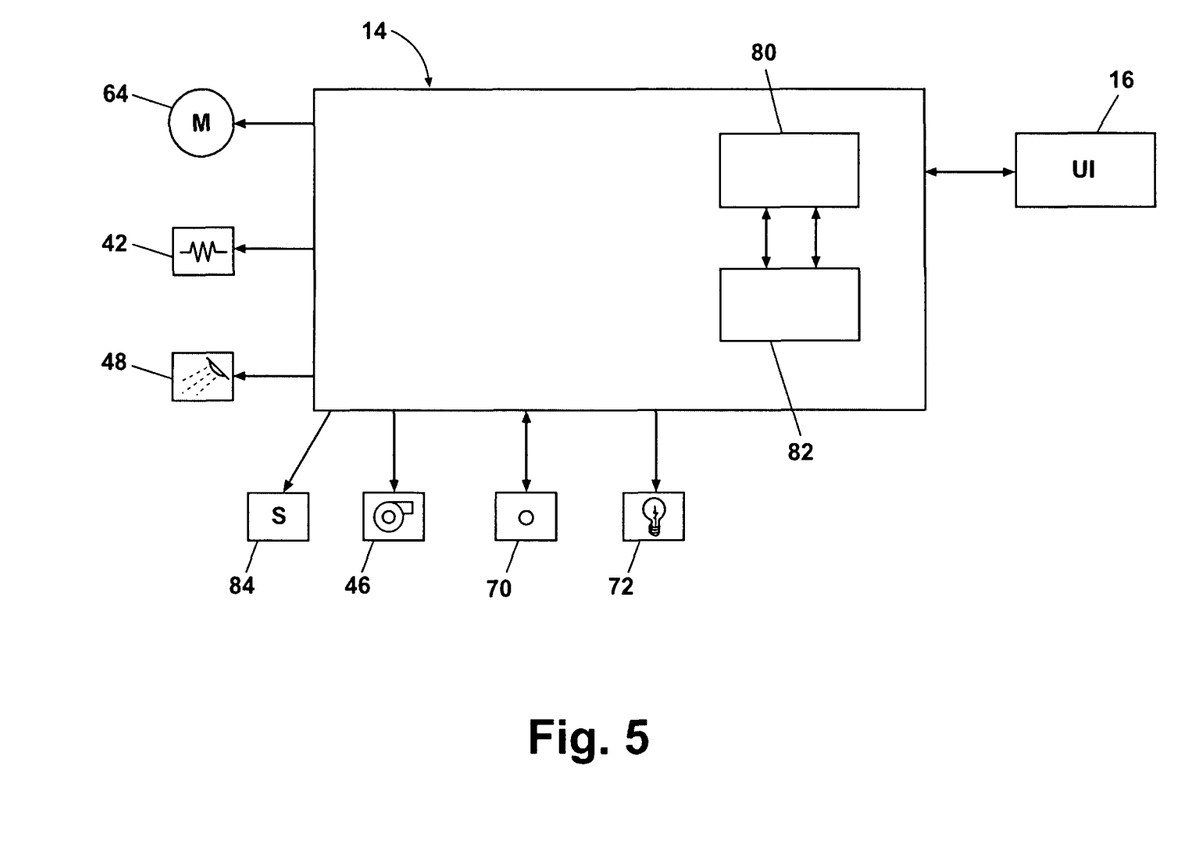
FIG. 5 is a schematic representation of a controller for controlling the operation of one or more components of the clothes dryer of FIG. 1 according to one embodiment of the invention.

As illustrated in FIG. 5, the controller 14 may be provided with a memory 80 and a central processing unit (CPU) 82. The memory 80 may be used for storing the control software that is executed by the CPU 82 in completing a cycle of operation using the clothes dryer 10 and any additional software. The memory 80 may also be used to store information, such as a database or table, and to store data received from the one or more components of the clothes dryer 10 that may be communicably coupled with the controller 14.

The controller 14 may be communicably and/or operably coupled with one or more components of the clothes dryer 10 for communicating with and controlling the operation of the component to complete a cycle of operation. For example, the controller 14 may be coupled with the heating element 42 and the blower 46 for controlling the temperature and flow rate through the treatment chamber 34; the motor 64 for controlling the direction and speed of rotation of the drum 28; and the dispensing system 48 for dispensing a treatment chemistry during a cycle of operation. The controller 14 may also be coupled with the user interface 16 for receiving user selected inputs and communicating information to the user.

The controller 14 may also receive input from one or more sensors 84, which are known in the art and not shown for simplicity. Non-limiting examples of sensors 84 that may by communicably coupled with the controller 14 include: a treating chamber temperature sensor, an inlet air temperature sensor, an exhaust air temperature sensor, a moisture sensor, an air flow rate sensor, a weight sensor, and a motor torque sensor.

The controller 14 may also be coupled with the imaging device 70 and illumination source 72 to capture one or more images of the treating chamber 34. The captured images may be sent to the controller 14 and analyzed using analysis software stored in the controller memory 80 to determine a fluffing state of the laundry. It is also contemplated that the image analysis may be performed by a separate processing system, or one integrated into the imaging device, and the results communicated with the controller. The controller 14 may use the determined fluffing state to set one or more operating parameters to control the operation of at least one component with which the controller 14 is operably coupled to complete a cycle of operation.

A brief description regarding the fluffing state of laundry may be useful in understanding the invention. During a treating process, it is common for liquid to be disposed on the surface of the laundry. In many cases, the laundry will have liquid on the surface as well as the interior of the laundry. As the laundry dries, a point will be reached where the surface is free from liquid. This point is commonly known as the fluffing state. That is, the fluffing state is when the surface is free of liquid regardless of whether there is liquid in the interior of the laundry. After reaching the fluffing state, the temperature of the laundry may begin to rise rapidly.

It has been found that the movement of the laundry items relative to each other or relative to the load may be used to indicate the condition of a fluffing state. However, the articles may begin relative movement before all of the liquid is removed across all of the surfaces of the articles. Therefore, the term fluffing state as used herein refers not only to the state where the surface of the laundry is free of liquid, it also refers to the condition where the surface of the laundry is sufficiently free of liquid to enable relative movement of the laundry.

In the case of the clothes dryer 10, the controller 14 may use an indication of a fluffing state to set one or more parameters of a treating cycle including a cycle step time, a cycle time, a cycle temperature, a direction of drum 28 rotation, a drum 28 rotational speed, an air flow rate in the treating chamber 34, a type of treating chemistry, a time to dispense a treating chemistry and an amount of treating chemistry.

In the case of a clothes washing machine, the fluffing state may be used to determine the load distribution during a wash or spin cycle. One or more parameters including a cycle step time, a cycle time, a direction of drum rotation, a drum rotational speed, a direction of agitator rotation, an agitator rotational speed, a wash liquid fill level, a type of treating chemistry, an amount of treating chemistry and a time to dispense a treating chemistry may be set according to the determined load distribution.

The previously described clothes dryer 10 provides the structure necessary for the implementation of the method of the invention. Several embodiments of the method will now be described in terms of the operation of the clothes dryer 10. The embodiments of the method function to automatically determine the fluffing state of the laundry load and control the operation of the clothes dryer 10 based on the determined fluffing state.

The fluffing state of the laundry may be determined by using the imaging device 70 to obtain one or more images over time of the contents of the drum 28 as it is rotating. The fluffing state of the laundry may then be used to control the operation of the clothes dryer 10.

Controlling the operation of the clothes dryer 10 based on the determined fluffing state may include setting at least one parameter of a cycle of operation including a cycle step time, a cycle time, a cycle temperature, a direction of drum rotation, a drum rotational speed, an air flow rate in a treating chamber 34, a type of treating chemistry, a time to dispense a treating chemistry and an amount of treating chemistry.

Setting a cycle step time may include determining the duration of a cycle step within a cycle of operation or determining when to start or end a cycle step. This may include signaling the controller 14 to immediately transition from one cycle step to another or setting a time at which to transition from one step to another within a given operating cycle. Examples of cycle steps include rotation with heated air, rotation without heated air, treatment dispensing, a wrinkle guard step.

Setting a cycle time may include determining the duration of a cycle of operation or determining when to start or end a cycle of operation. This may include signaling the controller 14 to immediately start or end a cycle of operation or setting a time at which to start or end a cycle of operation.

For laundry treating appliances other than clothes dryers, parameters of a cycle of operation that may be set based on the determined fluffing state may also include a rotational speed of an agitator, a direction of agitator rotation, and a wash liquid fill level.

Figure 6:
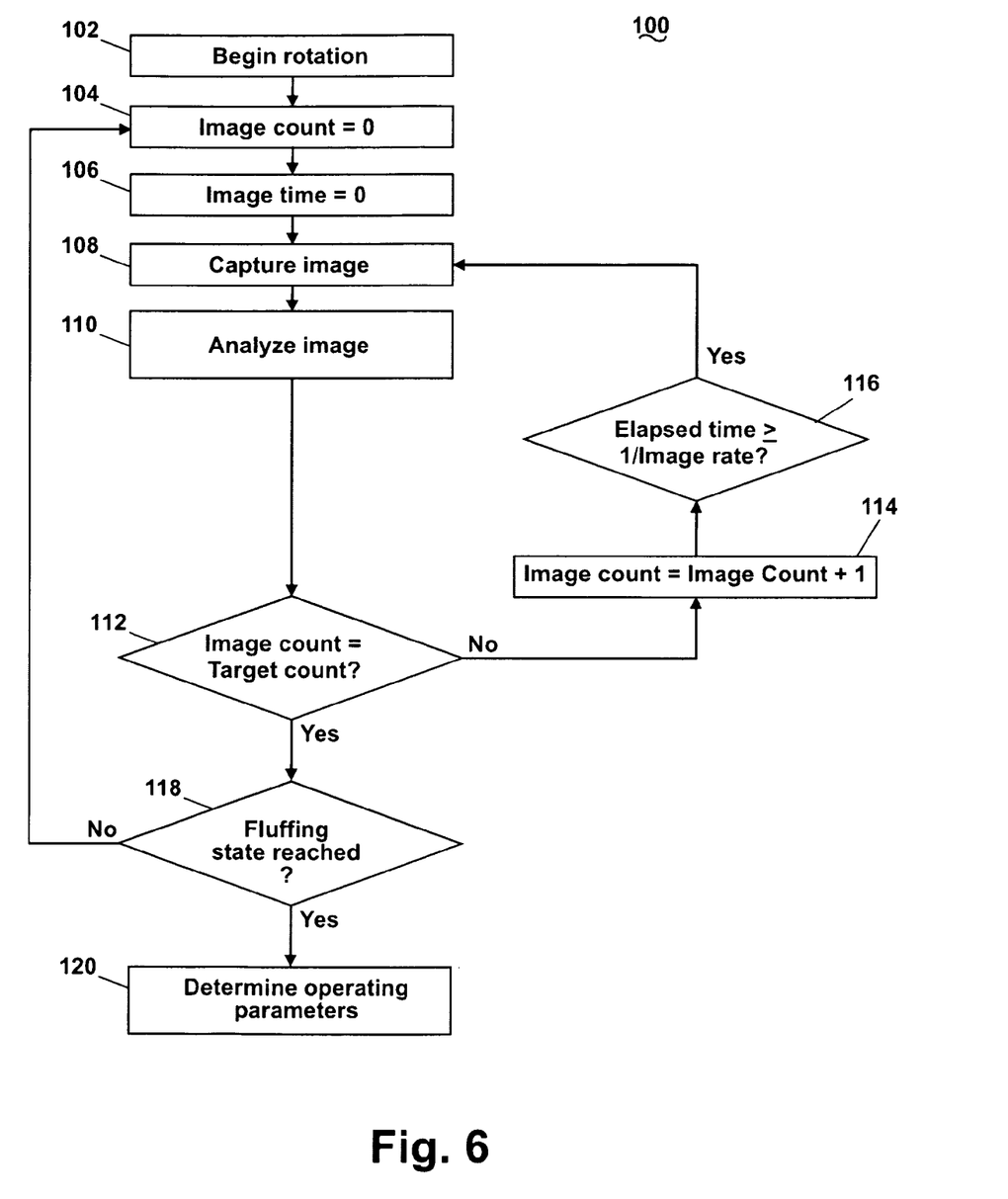
FIG. 6 is a flow chart illustrating a method for capturing and analyzing images of the treating chamber to determine a fluffing state according to a second embodiment of the invention.

Referring to FIG. 6, a flow chart of one method 100 of determining the fluffing state of a load of laundry is shown in accordance with the present invention. The fluffing state determining method 100 may be executed by the controller 14 during a drying or treatment cycle of the clothes dryer 10. The sequence of steps depicted is for illustrative purposes only, and is not meant to limit the fluffing determining method 100 in any way as it is understood that the steps may proceed in a different logical order or additional or intervening steps may be included without detracting from the invention.

The method 100 starts with assuming that the user has loaded the clothes dryer 10 with one or more articles to form the laundry load and closed the door 26. The method 100 may be initiated automatically, such as when the user closes the door 26, for example, or at the start of a user selected operating cycle.

In the step 102, the rotation of the drum 28 is initiated and the image count of a counter, which tracks the number of images taken, is set to 0 at step 104. Ultimately, the number of images counted by the counter is used to determine when to terminate the imaging of the laundry. The speed of rotation of the drum 28 may be increased until it reaches a predetermined speed of rotation. The predetermined speed of rotation may be determined by the controller 14 based on the selected operating cycle and the operating parameter settings. When the drum speed reaches the predetermined speed, the image time may be set to 0 at step 106 and the imaging device 70 may capture an image of all or some portion of the treating chamber 34. Alternatively, the image time may be set to 0 in step 106 after a predetermined amount of time has elapsed or after a predetermined step in a cycle of operation.

The one or more images captured in step 108 may be sent to the controller 14 for image analysis in step 110 using software that is stored in the memory 80 of the controller 14. It is also within the scope of the invention for the imaging device 70 to have a memory and a microprocessor for storing information and software and executing the software, respectively. In this manner, the imaging device 70 may analyze the captured image data and communicate the results of the analysis with the controller 14.

In step 110, analyzing the image may include separating the load image from the background, i.e. the dryer drum 28, in the image captured in step 108. Any suitable method may be used to separate the load from the background in the image. There are several methods for separating the load image from the background depending on the illumination configuration, drum properties and the load. Once the load image is separated from the background, an image of the treating chamber 34 may be created wherein each pixel in the image indicates the presence or absence of the load. The image separation techniques may also be used to separate one load item from another.

For example, in the case of an illumination configuration where the illumination source 72 is located on the same side of the drum 28 as the imaging device 70, techniques such as edge detection, color segmentation and deviation from a known background image may be used to separate the load from the background. Edge detection may be calculated using known methods. Color segmentation involves separating the individual items in a load from each other and separating the load from the background based on differences in the saturation, hue and luminance of objects in the image. The surface of the dryer drum 28 may also contain optically detectable features to aid in the separation of the load from the background image of the drum 28.

In the case of an illumination configuration in which the load is back lit from an illumination source 72 located on a portion of the drum 28 opposite from the imaging device 70, separation of the load from the background is simplified. The areas in which a load is present will appear black or dark in the image, since light from the illumination source 72 is blocked by the load. In places where the load is not present, the light from the illumination source may be detected by the imaging device 70.

Regardless of how the load image is separated from the background, the images captured by the imaging device 70 may be used to obtain information relating to the geometry of the laundry load relative to the drum 28 during image analysis in step 110. For example, the image may be used to calculate geometry parameters, such as the volume, size, area, perimeter, center of mass, radius, distance between load items and the major or minor axis of the load using known methods.

One method for determining the geometry parameters of the load may involve applying a grid to the image and analyzing the load relative to the grid. Non-limiting examples for use of the grid include: use as a coordinate system, especially to assess location within or relative to the treating chamber; for estimating size, area and volume; as well as a tool for estimating shapes or perimeters. In estimating size, area, and volume, the number of grid elements in which the load is present may be used, which may be compared to empirical data to improve the estimation The load position at any instant in time may be characterized by the number of grid elements in which the load is present, especially relative to the entire grid. Additionally, the percent coverage of the load in each grid element may be analyzed. The percent coverage is the percentage of pixels in the image where the load is present.

The number of grid elements in which the load is present for each image may be used to create a database from which one or more geometry parameters of the load may be determined. The geometry parameters for each image may be stored in a database of load geometry parameters in a memory accessible by the controller 14 such as the controller memory 80.

The stored geometry parameters may be used by the controller 14 to determine when one or more items of the load begin to move independently or when the size of the load has increased significantly, indicative of a fluffing state. This may include comparing the determined geometry parameters of the load in consecutive images to determine if one or more parameters have changed. Alternatively, the determined geometry parameters may be integrated over time to characterize the geometry of the load over a predetermined amount of time.

One benefit of using a grid is that the CCD or CMOS cameras have a sensor comprising multiple pixels, which form a grid-like structure. A single pixel or a grouping of pixels may be used to form a grid element.

In the next step 112, the controller 14 determines if the image count equals the target count. If the image count is less than the target count, the image count is increased by 1 in step 114. If the elapsed time is equal to or greater than one divided by the imaging rate at step 116, the method may return to step 108 and steps 108 through 112 may be repeated. Each time an image is captured and analyzed, the geometry parameters may be stored in the database for analysis in step 118 to determine if a fluffing state has been reached.

The target image count is selected such that a sufficient number of images may be captured and analyzed to determine if a fluffing state exists. The image rate is selected such that a predetermined number of images may be captured within a predetermined amount of time. The predetermined amount of time for capturing images for analysis may be set such that the fluffing state may be determined and appropriate action taken within a suitable amount of time to avoid or minimize damage to the fabric of the load.

If the image count equals the target count, then the geometry parameters of the load determined for each image and stored in the database may be analyzed to determine if a fluffing state has been reached in step 118. This may include comparing a determined geometry parameter of the load image, such as the radius, between images over time to determine if a change has occurred indicative of a fluffing state.

Several methods may be used in step 118 to determine if the change in one or more geometry parameters indicates a fluffing state. One method may include determining the difference in a geometry parameter between successive images. If the determined difference is greater than some predetermined threshold, the controller 14 may determine that one or more load items are beginning to move independently and that a fluffing state has been reached. Another method may include determining the rate of change of a geometry parameter over time. If the rate of change starts to increase, the controller 14 may determine that one or more items are beginning to move independently and that a fluffing state has been reached.

The threshold for determining that the movement of one or more items of the load or the size of the load indicates a fluffing state may vary depending on the size and fabric type of the load and the operating cycle. This may include setting a threshold based on a predetermined number of items moving independently or a predetermined amount or rate of change in one or more geometry parameters.

If it is determined that a fluffing state has been reached in step 118, the controller 14 may control the operation of the clothes dryer 10 based on the determined fluffing state in step 120. This may include setting at least one parameter of a cycle of operation including a cycle step time, a cycle time, a cycle temperature, a direction of drum 28 rotation, a drum 28 rotational speed, an air flow rate in a treating chamber 34, a type of treating chemistry, a time to dispense a treating chemistry and an amount of treating chemistry.

For example, if it is determined that a fluffing state has been reached, the controller 14 may turn off the heating element 42 and set the blower 36 and motor 64 to continue the flow of air through the treating chamber 34 and rotation of the drum 28 for a predetermined amount of time prior to ending the cycle of operation. In another example, once the fluffing state has been reached, the controller 14 may control the dispensing system 48 to dispense an anti-wrinkle treatment and set a time for ending the cycle of operation.

The controller 14 may also use the determination of a fluffing state to determine one or more of the following steps: when to add a treating chemistry, when enough treating chemistry has been added and when to end a drying cycle of operation after a treating chemistry has been dispensed. For example, if it is determined that a fluffing state has been reached, the controller 14 may control the dispensing system 48 to dispense a treating chemistry until the surface of the load is substantially saturated with the treating chemistry. As the surface of the load becomes saturated with the treating chemistry, the relative movement and/or size of the load may change, indicating that the determined fluffing state no longer exists. The controller 14 may stop dispensing the treating chemistry when it is determined that the load is no longer in the fluffing state. After the treatment step, a drying cycle can be continued until the load returns to the fluffing state, indicating that the surface of the load is again substantially free of liquid.

In addition to setting one or more parameters of a cycle of operation based on the determined fluffing state, the controller 14 may also use information received from one or more sensors 84. For example, an exhaust air temperature sensor may register a rise in the exhaust temperature indicating that less water is being evaporated from the load. In another example, a contact moisture sensor may be used to determine that little or no moisture is being removed from the load. The data from these types of sensors may be used in combination with the data obtained from the imaging device 70 for confirming the determination of the imaging system regarding the presence of a fluffing state. Additionally, these types of sensor may be used to initiate the imaging system for determining the fluffing state of the load.

If a fluffing state has not been reached, the steps 104 through 118 may be repeated until the controller 14 determines that a fluffing state has been reached.

Figure 7:
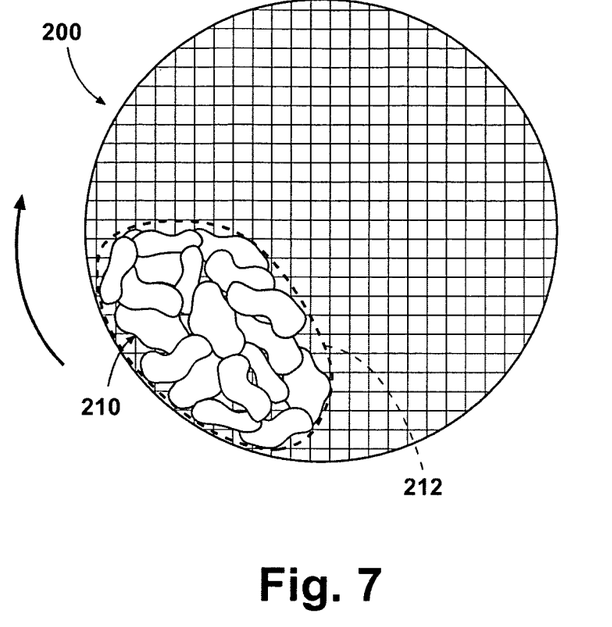
FIG. 7 is a schematic representation of an image of the treating chamber wherein the laundry is generally moving as a single cluster of items according to the second embodiment of the invention.

FIG. 7 is a schematic illustrating an example of an image 200 of the treating chamber 34 having a load 210 within the drum 28 as it is rotating clock-wise that may be captured using the method 100 as illustrated in FIG. 6. The image 200 is a schematic representation of a two-dimensional projection of what the imaging device 70 may actually see for the purposes of illustration. The image 200 may be captured according to step 108 and analyzed in step 110 by dividing the image 200 into multiple segments to create a grid extending from the periphery of the drum 28 into the center of the treating chamber 34. The location, number, shape and size of the grid elements may vary depending on a variety of factors, including, without limitation, the shape of the drum 28 and the location of the imaging device 70. It is within the scope of the invention for the captured image and applied grid to have any regular or irregular shape.

The load 210 may be formed from one or more load items of various size and shape. Early in the drying process, when liquid may be disposed on the surface of the load 210, the load 210 may travel as a cluster within the drum 28 as it is rotating. The items of the load 210 may travel as a single cluster due to a frictional force between individual items as a result of the residual liquid on the surface of the load items. The image 200 may be analyzed to determine one or more geometry parameters of the load 210 at a given instant in time. Alternatively, the geometry parameters from the image 200 may be integrated over time with the geometry parameters from one or more preceding or subsequent images to determine the geometry parameters for the load 210 over a predetermined period of time.

One method for determining if a fluffing state exists may involve determining the size of the load 210. For example, the size of the load 210 may be estimated by determining the number of grid elements in which the load is present. As the load 210 approaches the fluffing state, the number of grid elements occupied by the load 210 illustrated in FIG. 7 may start to increase.

If the difference in the number of grid elements occupied by the load 210 between consecutive images is greater than some predetermined threshold, it may be determined that the expansion in the size of the load 210 is indicative of a fluffing state. Alternatively, the number of grid elements in which the load 210 is present for multiple images may be used to determine the slope or rate of change in the size of the load 210 over time. The rate of change of the load size may then be used to determine when a fluffing state has been reached.

The presence of the load 210 may be determined using edge detection methods, for example, or based on the known properties of an interior surface of the drum 28 which makes up the background in the image. For example, each pixel in the image 200 may be represented by one or more numerical values indicative of the color of the image 200 at that pixel. The items of the load 210 may be identified based on the difference in pixel values between the load item and the known pixel values of the interior surface of the drum 28.

The determined presence of the load may also be used to define an effective outer boundary of the load 210. The grid elements in which the presence of the load 210 in the image 200 has been identified may be used to define an effective outer boundary or perimeter 212 in FIG. 7. The change or rate of change in the effective outer boundary may be used to determine the existence of a fluffing state.

Figure 8:
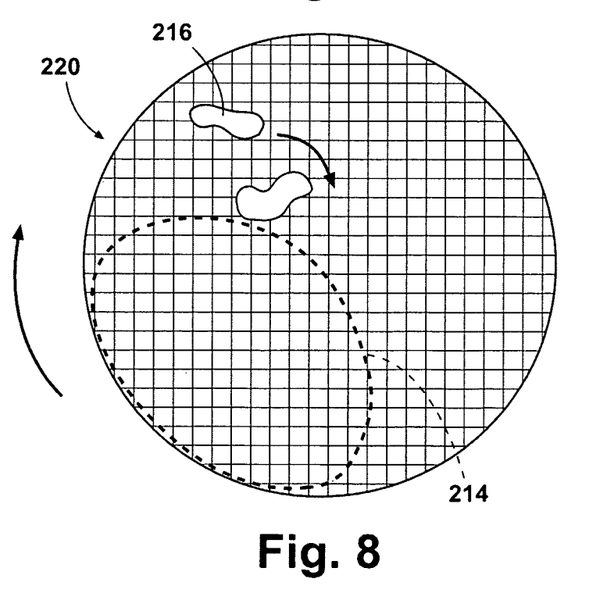
FIG. 8 is a schematic representation of an image of the treating chamber wherein the items of the laundry are starting to move independently from one another according to the second embodiment of the invention.

FIG. 8 illustrates an image 220 of the load 210 within the drum 28 as it is rotating clock-wise that may be captured at some point in time after the image 200 in which some or all of the liquid on the surface of the load 210 may have evaporated and the frictional force holding the load items together is decreasing. As the liquid on the surface evaporates, i.e. as the fluffing state is approached, the size of the load 210 may increase and one or more items of the load 210 may start to separate from the remainder of the load 210, resulting in an increase in the overall size or volume of the load.

The effective boundary 214 of the load 210 in FIG. 8 may be determined in the same manner as described above with regards to FIG. 7. As may be seen by comparing the effective boundary 212 in FIG. 7 and the effective boundary 214 in FIG. 8, the size of the load is increasing between images 200 and 220. The effective boundaries 212 and 214 may be compared by calculating one or more parameters defined by the effective boundaries 212 and 214 such as the area or the perimeter. If the effective boundary 214 is larger than the effective boundary 212 by some predetermined threshold value, it may be determined that a fluffing state exists. Alternatively, the effective boundary for multiple images may be determined over time and a fluffing state identified based on the rate of change of the effective boundary over a predetermined amount of time.

As illustrated in FIG. 8, as the load 210 approaches the fluffing state, one or more items of the load 210 may start to separate from the load 210 and move independently. For example, as an item 216 begins to move separately from the load 210, it may be lifted as the drum 28 rotates to a position between 10 and 11 o'clock and then fall back to the bottom of the drum 28. As the item 216 is lifted by the rotation of the drum 28, it separates from the rest of the load 210 defined by the effective outer boundary 214.

The movement of items outside the effective boundary 214 of the load 210 may be used to determine when a fluffing state has been reached. This may include determining that the number of items moving outside the effective boundary 214 is greater than some predetermined threshold or that the rate at which items are identified as moving outside the effective boundary is greater than some predetermined threshold.

In another example, independent movement of one or more items relative to the load 210 may be determined by determining the space between individual items of the load 210. Identification of the items of the load 210 may involve using any of the previously described methods. The distance between individual items may then be determined by counting the number of empty grid elements between grid elements in which the load 210 is present. As one or more items of the load 210 start to separate from the load 210 and move independently, the number of empty grid elements between items of the load 210 may increase.

A fluffing state may be determined when the average maximum distance between items of the load 210 has reached a predetermined threshold value or when the maximum distance for a single item of the load has reached a predetermined threshold. Alternatively, the rate of change of the distance between load items may also be used to determine that a fluffing state has been reached.

It is within the scope of the invention for each of these methods for analyzing the image data captured by the image device 70 to be used alone or in combination with one or more other methods. This may include integrating the percent coverage of the load 210 in each grid element over time for some predetermined amount of time to determine the area within which the load 210 is primarily located.

While the invention has been specifically described in connection with certain specific embodiments thereof, it is to be understood that this is by way of illustration and not of limitation. Reasonable variation and modification are possible within the scope of the forgoing disclosure and drawings without departing from the spirit of the invention which is defined in the appended claims. For example, the sequence of steps depicted in each method described herein is for illustrative purposes only, and is not meant to limit the disclosed methods in any way as it is understood that the steps may proceed in a different logical order or additional or intervening steps may be included without detracting from the invention.

What is claimed is:

1. A method for controlling an operation of a laundry treating appliance comprising a rotatable drum at least partially defining a treating chamber for receiving laundry for treatment in accordance with a treating cycle of operation, the method comprising:
   imaging the laundry to generate image data, the laundry comprising multiple articles;
   determining a change in a collective size of the laundry based on the image data; and
   determining a state of dryness where the surface of the laundry is free of liquid based on the determined change in the collective size of the laundry.

2. The method according to claim 1, further comprising setting at least one parameter of the treating cycle of operation based on the determined state of dryness.

3. The method according to claim 2 wherein the at least one parameter is one of a cycle step time, a cycle time, a cycle end time, a cycle step end time, a cycle temperature, a direction of drum rotation, a drum rotational speed, an air flow rate in the treating chamber, a direction of agitator rotation, an agitator rotational speed, a wash liquid fill level, a type of treating chemistry, a time to dispense a treating chemistry or an amount of treating chemistry.

4. The method according to claim 1, further comprising selecting at least a step of operation for the treating cycle of operation based on the determined state of dryness.

5. The method according to claim 4 wherein the selecting at least a step of operation comprises selecting a cycle of operation.

6. The method according to claim 1, further comprising dispensing a treating chemistry into the treating chamber, wherein at least one of a type, time to dispense or amount of the treating chemistry is selected based on the determined state of dryness.

7. The method according to claim 6, further comprising dispensing the treating chemistry in response to the determined state of dryness.

8. The method according to claim 7 wherein the treating chemistry is dispensed until the determined state of dryness is no longer present.

9. The method according to claim 8 wherein a drying cycle of operation is continued until the determined state of dryness returns.

10. The method according to claim 1, further comprising terminating at least one of the treating cycle of operation or a step in the treating cycle of operation in response to the determined state of dryness.

11. The method according to claim 10 wherein the at least a step of the treating cycle of operation comprises at least one of: a heating step, an air flow step, a dispensing step, or a rotational step.

12. The method according to claim 1 wherein the imaging comprises taking at least one of a still image or a moving image.

13. The method according to claim 12 wherein the imaging comprises capturing a digital image.

14. The method according to claim 1 wherein the imaging comprises taking at least one of a visible light image, an ultraviolet light image or an infrared image.

15. The method according to claim 1 wherein the state of dryness is indicative of the surface of the laundry being substantially free of liquid.

16. The method according to claim 1 wherein the determining a change comprises determining at least one of an absolute change or a time rate of change.

17. The method according to claim 3 wherein setting the at least one of a cycle end time and a cycle step end time comprises setting an end time for at least one of: a heating step, an air flow step, a dispensing step or a rotational step.

18. A method for controlling an operation of a laundry treating appliance comprising a rotatable drum at least partially defining a treating chamber for receiving laundry for treatment in accordance with a treating cycle of operation, the method comprising:
   imaging the laundry to generate image data, the laundry comprising multiple articles;
   determining a change in a relative movement of the articles forming the laundry based on the image data; and
   determining a state of dryness where the surface of the laundry is free of liquid based on the determined change in the relative movement of the articles forming the laundry.

19. The method according to claim 18, further comprising setting at least one parameter of the treating cycle of operation based on the determined state of dryness.

20. The method according to claim 19 wherein the at least one parameter is one of a cycle step time, a cycle time, a cycle end time, a cycle step end time, a cycle temperature, a direction of drum rotation, a drum rotational speed, an air flow rate in the treating chamber, a direction of agitator rotation, an agitator rotational speed, a wash liquid fill level, a type of treating chemistry, a time to dispense a treating chemistry or an amount of treating chemistry.

21. The method according to claim 20 wherein setting the at least one of a cycle end time and a cycle step end time comprises setting an end time for at least one of: a heating step, an air flow step, a dispensing step or a rotational step.

22. The method according to claim 19, further comprising selecting at least a step of operation for the treating cycle of operation based on the determined state of dryness.

23. The method according to claim 22 wherein the selecting at least a step of operation comprises selecting a cycle of operation.

24. The method according to claim 18, further comprising dispensing a treating chemistry into the treating chamber, wherein at least one of a type, time to dispense or amount of the treating chemistry is selected based on the determined state of dryness.

25. The method according to claim 24, further comprising dispensing the treating chemistry in response to the determined state of dryness.

26. The method according to claim 25 wherein the treating chemistry is dispensed until the determined state of dryness is no longer present.

27. The method according to claim 26 wherein a drying cycle of operation is continued until the determined state of dryness returns.

28. The method according to claim 18, further comprising terminating at least one of the treating cycle of operation or a step in the treating cycle of operation in response to the determined state of dryness.

29. The method according to claim 28 wherein the at least a step of the treating cycle of operation comprises at least one of: a heating step, an air flow step, a dispensing step, or a rotational step.

30. The method according to claim 18 wherein the imaging comprises taking at least one of a still image or a moving image.

31. The method according to claim 30 wherein the imaging comprises capturing a digital image.

32. The method according to claim 18 wherein the imaging comprises taking at least one of a visible light image, an ultraviolet light image or an infrared image.

33. The method according to claim 18 wherein the state of dryness is indicative of the surface of the laundry being substantially free of liquid.

34. The method according to claim 18 wherein the determining a change comprises determining at least one of an absolute change or a time rate of change.

35. A method for controlling an operation of a laundry treating appliance comprising a rotatable drum at least partially defining a treating chamber for receiving laundry for treatment in accordance with a treating cycle of operation, the method comprising:
   imaging the laundry to generate image data;
   determining a change in a separation of an article from a collection of articles forming the laundry based on the image data; and
   determining a state of dryness where the surface of the laundry is free of liquid based on the determined change in the separation of an article from the collection of articles forming the laundry.

36. The method according to claim 35, further comprising setting at least one parameter of the treating cycle of operation based on the determined state of dryness.

37. The method according to claim 36 wherein the at least one parameter is one of a cycle step time, a cycle time, a cycle end time, a cycle step end time, a cycle temperature, a direction of drum rotation, a drum rotational speed, an air flow rate in the treating chamber, a direction of agitator rotation, an agitator rotational speed, a wash liquid fill level, a type of treating chemistry, a time to dispense a treating chemistry or an amount of treating chemistry.

38. The method according to claim 37 wherein setting the at least one of a cycle end time and a cycle step end time comprises setting an end time for at least one of: a heating step, an air flow step, a dispensing step or a rotational step.

39. The method according to claim 35, further comprising selecting at least a step of operation for the treating cycle of operation based on the determined state of dryness.

40. The method according to claim 39 wherein the selecting at least a step of operation comprises selecting a cycle of operation.

41. The method according to claim 35, further comprising dispensing a treating chemistry into the treating chamber, wherein at least one of a type, time to dispense or amount of the treating chemistry is selected based on the determined state of dryness.

42. The method according to claim 41, further comprising dispensing the treating chemistry in response to the determined state of dryness.

43. The method according to claim 42 wherein the treating chemistry is dispensed until the determined state of dryness is no longer present.

44. The method according to claim 43 wherein a drying cycle of operation is continued until the determined state of dryness returns.

45. The method according to claim 35, further comprising terminating at least one of the treating cycle of operation or a step in the treating cycle of operation in response to the determined state of dryness.

46. The method according to claim 45 wherein the at least a step of the treating cycle of operation comprises at least one of: a heating step, an air flow step, a dispensing step, or a rotational step.

47. The method according to claim 35 wherein the imaging comprises taking at least one of a still image or a moving image.

48. The method according to claim 47 wherein the imaging comprises capturing a digital image.

49. The method according to claim 35 wherein the imaging comprises taking at least one of a visible light image, an ultraviolet light image or an infrared image.

50. The method according to claim 35 wherein the state of dryness is indicative of the surface of the laundry being substantially free of liquid.

51. The method according to claim 35 wherein the determining a change comprises determining at least one of an absolute change or a time rate of change.

* * * * *